United States Patent
Bosma et al.

(10) Patent No.: US 7,316,200 B2
(45) Date of Patent: Jan. 8, 2008

(54) METHOD AND DEVICE AT A DAIRY FARM

(75) Inventors: Epke Bosma, Tumba (SE); Nils Erik Holmertz, Huddinge (SE); Lars Wase, Danderyd (SE); Lars Gullander, Stigtomta (SE)

(73) Assignee: Delaval Holding AB, Tumba (SE)

( * ) Notice: Subject to any disclaimer, the term of this patent is extended or adjusted under 35 U.S.C. 154(b) by 408 days.

(21) Appl. No.: 10/518,899

(22) PCT Filed: Jul. 4, 2003

(86) PCT No.: PCT/SE03/01169

§ 371 (c)(1),
(2), (4) Date: Dec. 22, 2004

(87) PCT Pub. No.: WO2004/004791

PCT Pub. Date: Jan. 15, 2004

(65) Prior Publication Data

US 2005/0223998 A1    Oct. 13, 2005

(30) Foreign Application Priority Data

Jul. 5, 2002   (SE) .................................. 0202112

(51) Int. Cl.
*A01K 13/00* (2006.01)
*A01J 7/02* (2006.01)
(52) U.S. Cl. .................. 119/14.08; 119/14.18
(58) Field of Classification Search ............ 119/14.08, 119/14.1, 14.18, 51.02, 520, 651, 665
See application file for complete search history.

(56) References Cited

U.S. PATENT DOCUMENTS 3,461,845 A * 8/1969 Peterson .................. 119/14.18
5,195,455 A * 3/1993 van der Lely et al. .... 119/14.03

(Continued)

FOREIGN PATENT DOCUMENTS

EP    0 800 763 A2   10/1997

(Continued)

OTHER PUBLICATIONS

"Minimized spread of infection between cows during milking", Disclosed anonymously, Research Disclosure, Publication No. 444037, Apr. 2001, p. 538.

*Primary Examiner*—Rob Swiatek
(74) *Attorney, Agent, or Firm*—Harness, Dickey & Pierce, P.L.C.

(57) ABSTRACT

A method of disinfecting or sterilizing at least a portion of any of a resting, a milking, or a feeding station (3, 24, 26) provided with an animal identification device (18) and located in an area (1), in which milking animals are allowed to move, is provided. Each of the animals visiting the resting, the milking, or the feeding station is identified and is admitted to enter the station depending on the identification. The inventive method comprises the steps of retrieving information regarding the health of each of the animals entering the station; and automatically disinfecting or sterilizing the portion of the station only if the information retrieved reveals that an animal entering the station has an infection that is capable of being transmitted to other animals. The disinfection or the sterilization is performed after that said infectious milking animal has left the station.

25 Claims, 5 Drawing Sheets

U.S. PATENT DOCUMENTS

| | | |
|---|---|---|
| 6,237,530 B1 * | 5/2001 | van der Lely et al. .... 119/14.08 |
| 6,267,077 B1 | 7/2001 | van den Berg et al. |
| 6,276,297 B1 | 8/2001 | van den Berg et al. |
| 6,279,507 B1 | 8/2001 | van der Lely et al. |

FOREIGN PATENT DOCUMENTS

| | | |
|---|---|---|
| EP | 1 099 373 A1 | 5/2001 |
| WO | WO 03/077645 A1 | 9/2003 |

* cited by examiner

| Cow No. | Time since last milking | Milking Priority | Time since last feeding | Milk production | Health |
|---------|-------------------------|------------------|-------------------------|-----------------|--------|
| . | . | . | . | . | . |
| . | . | . | . | . | . |
| . | . | . | . | . | . |
| 21 | 38 | 8 | 175 | 27 | 1 |
| 22 | 240 | 98 | 30 | 65 | 1 |
| 23 | 137 | 48 | 150 | 45 | 1 |
| 24 | 292 | 90 | 110 | 38 | 2 |
| 25 | 68 | 18 | 123 | 30 | 1 |
| 26 | 103 | 26 | 79 | 40 | 1 |
| 27 | 1 | 0 | 160 | 78 | 3 |
| . | . | . | . | . | . |
| . | . | . | . | . | . |
| . | . | . | . | . | . |

Fig. 4

METHOD AND DEVICE AT A DAIRY FARM

TECHNICAL FIELD OF THE INVENTION

The present invention relates to dairy farming, and to disinfection and sterilization related thereto.

DESCRIPTION OF RELATED ART AND BACKGROUND OF THE INVENTION

When a milking animal, such as a cow, presents herself for milking it is important to ensure that the teat cups to be attached to the teats of the milking animal are clean and free of any condition that could contaminate the teats of the milking animal. Therefore, it is customary to clean the teat cups between milkings of milking animals, where either a cleaning liquid or pure water is used.

It is also customary, for the same reason, to clean the teats of each milking animal prior to the attachment of the teat cups. For teat cleaning, dedicated teat cleaning cups or brushes may be employed.

However, while such cleaning removes dirt from the teats and provides for an overall hygienic environment, there is nevertheless a risk of communicating infections, such as for instance mastitis, from one animal to another.

In Research Disclosure, April 2000, publication No. 444037, p. 530, it is proposed to spray the surfaces of the teat cups and the teat cleaning cups that potentially are exposed to the animals with hot steam to heat up the surfaces to a temperature, at which bacteria are killed. It is also proposed to illuminate the surfaces with UV light.

In U.S. Pat. No. 6,267,077 is described to employ a rinsing liquid with an additive, such as sodium hypochlorite, via supply lines and spray nozzles to clean and disinfect components of a milking machine, such as a cleaning member and a robot arm.

In U.S. Pat. No. 6,276,297 is disclosed a disinfecting device that disinfects those parts of a milking equipment and of a cleaning device which contact the teats and also usually the udder of an animal to be milked. The disinfecting device comprises an ultraviolet light source for destroying harmful bacteria by means of exposing them to UV radiation.

SUMMARY OF THE INVENTION

The known disinfecting techniques are all energy and time consuming being used at an automatic milking machine to ensure that no infections are transmitted from animal to animal. The high energy needed results in an inefficient disinfection or sterilization process, and the time delays introduced by the process result in an inefficient utilization of the milking machine, and as an automatic milking machine involves heavy expenditure and has a limited milk production capacity, such time delays may not be acceptable.

Further, an infection may be transmitted from animal to animal at other places in a dairy farm. For instance, when milking animals are lying down in a resting stall small amounts of milk may leak, and as a consequence there is a risk of infection via the resting stalls. Besides, the inventors believe that surfaces of a feeding stall, which an animal may come into contact with, e.g. a feeding device such as a feeding manger, may be a source for transmission of infections.

Accordingly, it is an object of the present invention to provide a method and a device, respectively for automatically disinfecting or sterilizing in an automated milking system, which overcome the above-identified problems associated with prior art.

It is in this respect a particular object of the invention to provide such a method and such a device that are effective, accurate, reliable, safe, and of low cost.

It is a further object of the invention to provide such a method and such a device that are easily implemented into existing dairy farm equipment.

These objects among others are attained by methods and devices as claimed in the appended patent claims.

By means of retrieving information regarding the health of each milking animal entering any of a resting, a milking, or a feeding station, and automatically disinfecting or sterilizing at least a portion of the station if the information as retrieved reveals that a milking animal entering the station has a transmittable infection, wherein the disinfection or the sterilization is performed after that the infectious animal has left the station, it can be safeguarded that no infections are transmitted via the station while the disinfection or the sterilization only has to be performed after a visit by an infectious animal. The at least portion of the station includes preferably surfaces that an infectious animal may come into contact with. Assuming that a large number of milking animals are healthy, the disinfection or the sterilization has only to be performed occasionally, and hence energy consumption is reduced and time is saved.

Preferably, a computer holding a database with information of the milking animals and their health is provided, wherein information regarding the health of each milking animal entering the station is retrieved by means of referring to the database. The information may be entered into the database manually, or may be entered automatically from a computer-connected measuring device for measuring a health-related parameter of the milking animals.

Still preferably, the station may be automatically disinfected or sterilized irrespective of the information retrieved if a particular time, e.g. a day or a week, has lapsed since last disinfection or sterilization of that station. This is to ensure that the milking station is disinfected or sterilized e.g. at least once a day or once a week even if all animals visiting the station are healthy in order to ensure a good hygiene in the station.

Yet preferably, the station may be automatically disinfected or sterilized irrespective of the information retrieved if (i) it is established that no milking animal visits or is to visit the station in the near future, and (ii) a particular time has lapsed since last disinfection or sterilization of that station or at least a portion thereof was performed. Such approach is advantageous since it does not reduce the utilization of the station. The second condition is there to prevent the station from being repeatedly disinfected or sterilized if the station is not visited by any milking animal for a longer time.

Still preferably, the station may be automatically disinfected or sterilized irrespective of the information retrieved, e.g. more often, if there is an infectious disease spread among the milking animals that have access to the station.

Yet preferably, each station that is provided with an animal identification device (including resting, feeding and milking stations) located in an area housing a herd of milking animals may be subjected to the disinfection or the sterilization. Consequently, all surfaces of the equipment an infectious animal in the area may contact for a specified purpose or accidentally shall be automatically disinfected or sterilized after the animal has been identified at, and subsequently left, that station.

Further characteristics of the invention, and advantages thereof, will be evident from the detailed description of embodiments of the present invention given hereinafter and the accompanying FIGS. 1-4, which are given by way of illustration only, and thus are not limitative of the present invention.

In the following detailed description the milk producing animals are cows. However, the invention is not limited to cows, but is applicable to any animals having the capability to produce milk, such as sheep, goats, buffaloes, horses, etc.

BRIEF DESCRIPTION OF THE DRAWINGS

FIG. 4 displays schematically an example of an extract of a database comprised in a processing device of the animal arrangement of FIG. 1.

DETAILED DESCRIPTION OF EMBODIMENTS

Figure 1:
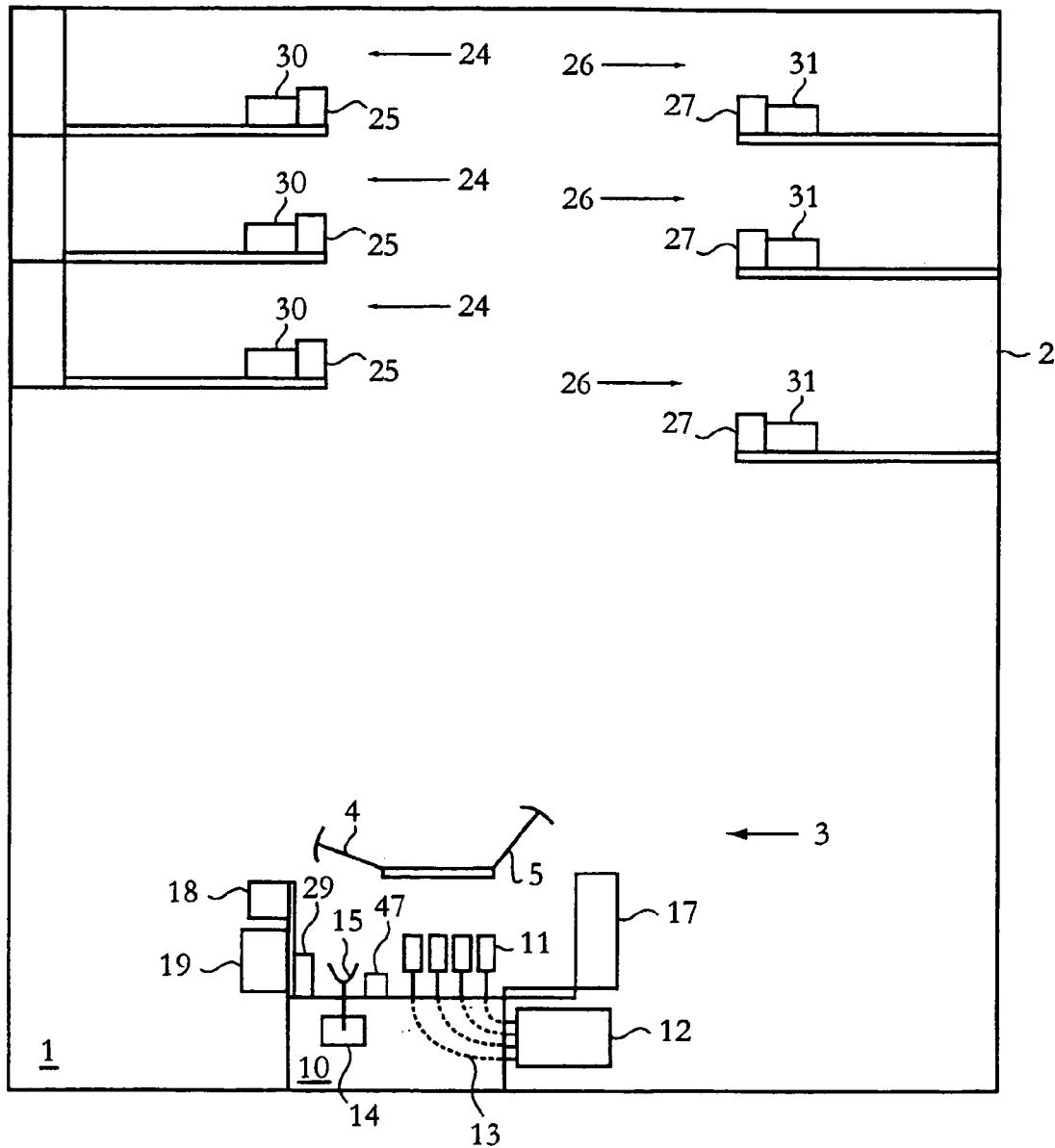
FIG. 1 illustrates, schematically, an arrangement for housing a herd of cows, wherein embodiments of the present invention are implemented.

FIG. 1. illustrates an animal arrangement for housing a herd of freely walking cows, which comprises an area 1 defined by enclosure means 2 in the shape of a fence, a grid or the like. In the area 1, there is provided a milking station 3 arranged for voluntary milking of the freely walking cows, i.e. the cows enter the milking station 3 in order to be milked when they want to. The milking station 3 comprises an enclosure having an inlet gate 4 and an outlet gate 5, which are both capable of being opened automatically.

The milking station 3 comprises further an automatic milking machine 10 including teat cups 11 connected to an end unit 12 by means of milk lines 13. The milking machine 10 includes a robot or automatic handling device 14 having an arm 15 provided with a gripper. The handling device 14 is arranged to automatically apply the teat cups 11 of the milking machine 10 to the teats of a cow present in the milking station 3 prior to milking.

Figure 2:
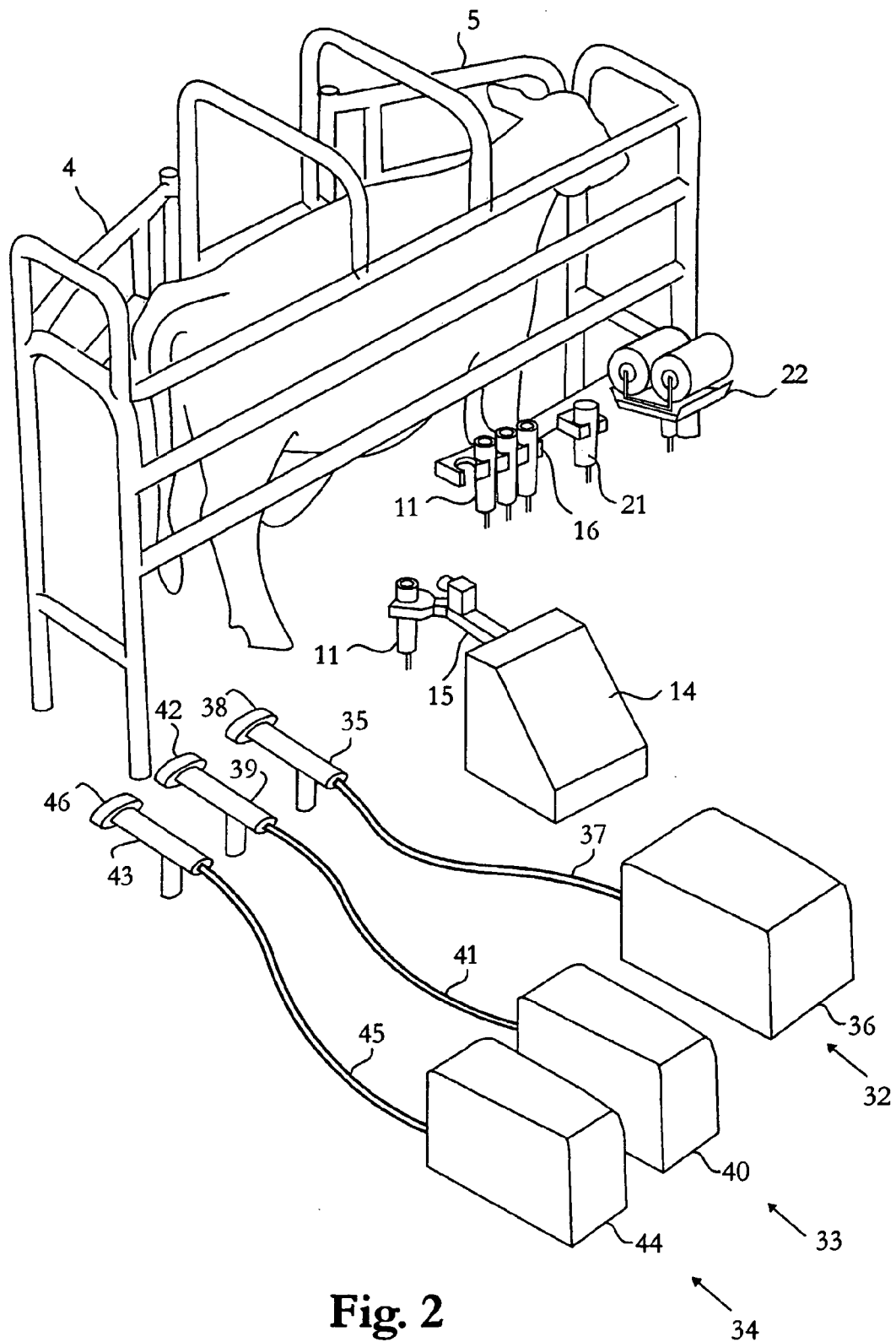
FIG. 2 illustrates, schematically, in a perspective view portions of an automated milking station as being comprised in the arrangement of FIG. 1.

In FIG. 2 portions of the milking station 3 are schematically illustrated in a perspective view. Three of the teat cups 11 are arranged in a teat cup rack or magazine 16, whereas the fourth one is held by the gripper of the arm 15.

Further, the milking station 3 may comprise a feeding device or manger 17 provided in the front end of the milking station 3, the purposes of which being to entice the cow to enter the milking station 3 for milking.

Still further, the milking station 3 comprises an identification member 18 provided to identify a cow approaching the milking station 3, and a central processing and control device 19, which is responsible for central processing and controlling of the animal arrangement, which inter alia includes the initiation of various activities in connection with the milking such as e.g. opening and closing of the gates 4 and 5, and control of the milking machine 10 and its handling device 14.

The central processing and control device 19 comprises typically a microcomputer, suitable software, and a database. An example of an extract of the database is illustrated in FIG. 4, wherein figures are given in arbitrary units. The database includes typically information of each of the cows in the area 1, such as e.g. when the respective cow was milked last time, when she was fed last time, her milk production, her health, etc. Particularly, the database may store information such as whether the respective cow has mastitis or any other infection, which of her teats being infected, etc. To this end, the sixth column of the database indicates whether a cow is healthy (1), has mastitis (2), or has another infection (3).

A cow approaching the milking station is thus identified by the identification member 18, and the central processing and control device 19 may then, depending on the identification, give the cow access to the milking station 3 by means of opening the inlet gate 4. The teats may be cleaned by a teat cleaning device such as a teat cleaning cup or brushes (not explicitly illustrated in FIG. 1, but shown as 21 and 22 in FIG. 2), whereafter the teat cups 19 are applied to the teats of the cow in the milking station 3.

During milking, milk is drawn from the teats of the cow by means of vacuum being applied to the teat cups 11. The milk drawn is collected in the end unit 12. After the milking has been completed the outlet gate 5 is opened and the cow may leave the milking station 3.

Each teat cup may be connected individually by means of the respective milk line 13 to the end unit 12, from which the milk is pumped to a cooled storage tank (not illustrated).

It shall be appreciated by the man skilled in the art that there may be provided one or several milking stations of the above-described kind in the area 1 of FIG. 1.

Furthermore, the area 1 may house one or several feeding stalls or stations 24, each being provided with a cow identification member 25 provided to identify a cow entering the respective feeding station 24 for eating and drinking. Each identification member 25 is connected individually to the central processing and control device 19 such that central processing and control device 19 at each instant can establish whether each feeding station 24 is being visited and by which cow.

Correspondingly, the area 1 may house one or several resting stalls or stations 26, each being provided with a cow identification member 27 provided to identify a cow entering the respective resting station 26 for resting. Each identification member 27 is connected individually to the central processing and control device 19 such that the central processing and control device 19 at each instant can establish whether each resting station 26 is occupied and by which cow.

The provisions described above provide for an effective and hygienic highly automated dairy farming facility with high milk production. Nevertheless, recent investigations may suggest that the cleaning performed is not effective regarding the spreading of microorganisms and bacteria, which may transfer infectious illnesses or infections from cow to cow in the area 1.

The milking station 3 of the animal arrangement of FIG. 1 is therefore provided with an apparatus 29 for disinfection and/or sterilization of various parts of the milking station 3 that a cow may contact for a specified purpose or accidentally, e.g. surfaces of the teat cups 11, the teat cleaning devices 21, 22, the manger 17, a front portion of the arm 15 of the handling device 14, the gates 4, 5, the walls and floor of the milking station 3.

Correspondingly, each feeding station 24 and each resting station 26 is provided with a respective apparatus 30, 31 for disinfection and/or sterilization of various parts of that station. Parts to be disinfected and/or sterilized may be inner walls, and the floor of the station and in case of a feeding station the manger/feeding device thereof may need to be disinfected and/or sterilized.

Each apparatus 29, 30, 31 for disinfection and/or sterilization is connected individually to the central processing and control device 19, which is responsible for the operation of the respective apparatus. Alternatively, each apparatus 29, 30, 31 is provided with a respective microprocessor for control of its operation, which microprocessor in turn is connected to the central processing and control device 19 for receiving commands from there.

Further, each apparatus 29, 30, 31 for disinfection and/or sterilization may use any of heat treatment, radiation or treatment with chemicals to render pathogenic microorganisms harmless or remove them. By disinfection is here meant rendering microorganisms such as bacteria, virus and pathogenic microscopic fungi harmless or remove them to such an extent that the treated objects or surfaces do not transmit infections, whether there is put a higher requirement on sterilization to render all microbes harmless.

In FIG. 2 is illustrated three different apparatuses 32, 33, 34 for disinfection and sterilization that may be used, by themselves or in any combination, as any of the apparatuses 29, 30, 31 as illustrated in FIG. 1.

The disinfection and/or sterilization apparatus 32 is based on heat treatment and includes an injector 35 connected to a hot fluid generator 36 via a supply tube 37. The injector 35 includes a nozzle 38, which preferably is adjustable. The hot fluid generator 36 may be adapted for generation of steam or hot air, which, during use, is flown through the tube 37 and out through the nozzle 38 as a jet towards an object, or part thereof, to be disinfected or sterilized.

The disinfection and/or sterilization apparatus 33 is based on use of chemicals or disinfectants such as an alcohol and includes an injector 39 connected to a supply unit 40 via a supply tube 41. The injector 39 includes a nozzle 42, which preferably is adjustable. The supply unit 40 is filled with a chemical or disinfectant, which, during use, is flown through the tube 41 and out through the nozzle 42 as a jet towards an object, or part thereof, to be disinfected or sterilized.

Finally, the disinfection and/or sterilization apparatus 34 is based on use of radiation for the disinfection or the sterilization and includes a radiation device 43, such as a UV laser source or an X-ray tube, connected to a power supply unit 44 via a cable 45. In front of the radiation device 43 there is arranged a collimator 46 or similar, which preferably is adjustable. During use, power is supplied to the radiation device 43 via the cable 45 and as a result the radiation device 43 generates UV light or X-rays, which via the collimator 46 is output from the radiation device 43 as a beam of radiation, which in turn is directed towards an object, or part thereof, to be disinfected or sterilized.

Any of the disinfection and/or sterilization apparatuses 32, 33, 34 may be handled by the handling device 14, or by other equipment (not illustrated) in order to position and direct the apparatuses 32, 33, 34 appropriately to reach objects/surfaces to be disinfected or sterilized.

Figure 5:
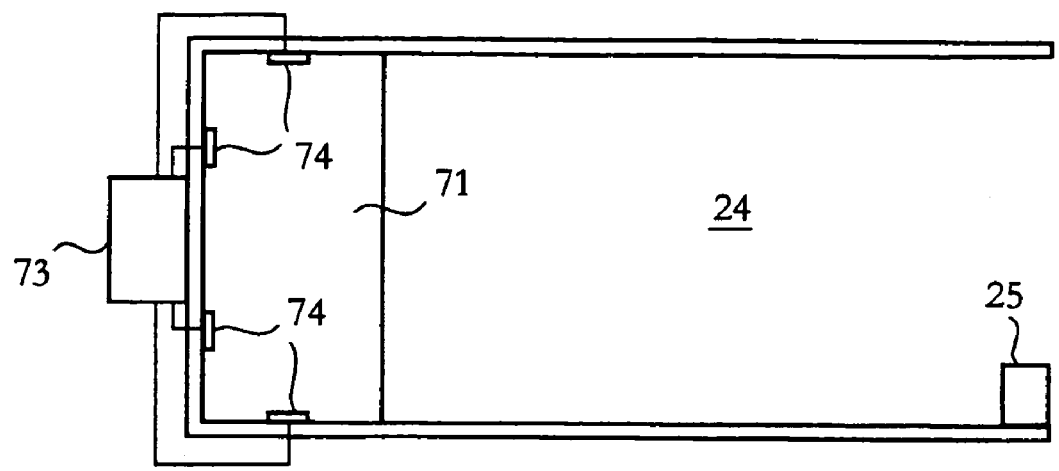
FIG. 5 illustrates, schematically, a feeding station wherein a further embodiment of the present invention is implemented.
Figure 6:
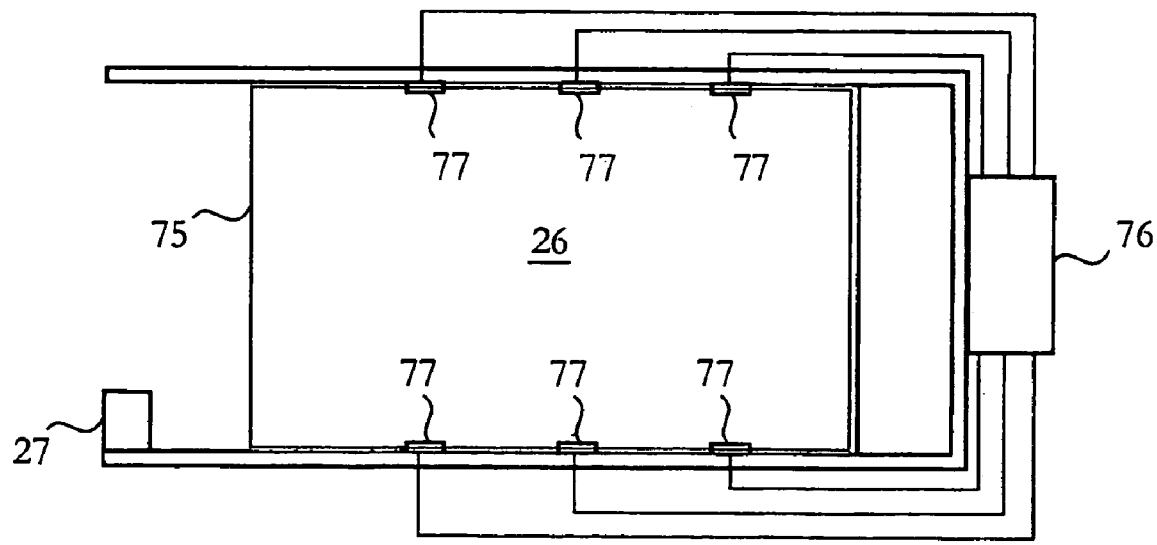
FIG. 6 illustrates, schematically, a resting station wherein still a further embodiment of the present invention is implemented.

FIGS. 5 and 6 illustrate schematically a feeding station and a resting station, respectively, in each of which a respective particular embodiment of the present invention is implemented.

The feeding station 24 of FIG. 5 includes a feeding device or manger 71 and a stationary disinfection/sterilization device 73 having four different supply lines, each of which ends in a nozzle 74 mounted in the wall of the feeding station 24. The nozzles 74 are oriented to direct any disinfection/sterilization agent as supplied by the disinfection/sterilization device 73 towards the manger 71 to effectively disinfect/sterilize it. In other respects the disinfection/sterilization device 73 may be connected and operated as any of the disinfection and/or sterilization apparatuses described above.

The resting station 26 of FIG. 6 includes a mat 75 to provide a softer and more comfortable bed for the resting cow. Further, a stationary disinfection/sterilization device 76 having six different supply lines is provided, where each of the supply lines ends in a nozzle 77 mounted in the wall of the resting station 26. The nozzles 77 are oriented to direct any disinfection/sterilization agent as supplied by the disinfection/sterilization device 76 towards the mat 75 to effectively disinfect/sterilize it. In other respects the disinfection/sterilization device. 76 may be connected and operated as any of the disinfection and/or sterilization apparatuses described above.

It shall be appreciated to the man skilled in the art that the disinfection and/or sterilization apparatuses described above are merely examples, and that virtually any kind of apparatus having the capability of disinfection or sterilization may be used in the present invention. In this regard reference is made to the technical field of disinfection and sterilization, and particularly to the documents referred to in the prior art section, i.e. Research Disclosure publication No. 444037, U.S. Pat. No. 6,267,077, and U.S. Pat. No. 6,276,297, as well as to our co-pending Swedish patent application No. 0200802-7, entitled Method and arrangement at a dairy farm, and filed on Mar. 22, 2002, the contents of which documents being hereby incorporated by reference.

Since disinfection and sterilization is energy and time consuming, and moreover large surfaces/objects have to be disinfected or sterilized in order to ensure that transmission of infectious illnesses and infections is impeded. To this end, the present inventors proposes to disinfect or sterilize equipment and surfaces that a cow has contacted or may have accidentally contacted only if some important conditions are met.

According to the present invention the processing and control device 19 is adapted to retrieve information regarding the health of each of the cows entering each station 3, 24, 26, and, provided that the information retrieved reveals that a cow entering any of the stations 3, 24, 26 has an infection that is capable of being transmitted to other cows, to control the respective disinfecting and/or sterilizing apparatus 29, 30, 31 to automatically disinfect or sterilize equipment/surfaces of that station 3, 24, 26, which the infectious cow may possibly have contacted, after that the cow has left the station 3, 24, 26.

Preferably, in order to ensure that no infection is transmitted from cow to cow each station located in the area 1 shall be provided with an animal identification device; and all surfaces of that station, which a cow in the area 1 may contact for a specified purpose or accidentally, shall be disinfected or sterilized after a visit by an infectious cow.

Still preferably, means are provided to ensure that no further cows are admitted to enter the station 3, 24, 26 until the disinfection or the sterilization has been terminated. In the milking station 3 this is ensured by having the inlet gate 4 closed. Similar inlet gates may be provided at each feeding 24 and resting 26 station.

The information regarding the health of each of the cows entering each station 3, 24, 26, which the processing and control device 19 is adapted to retrieve, may be information held in the database such as whether the respective cow has mastitis or any other infection, which of her teats being infected, etc. The information may have been entered into the database manually e.g. by the farmer, or it may have been communicated automatically to the central processing and control device 19, wherafter the central processing and control device 19 updates the database.

For instance, the central processing and control device 19 may be electronically connected to e.g. a laboratory, to which milk samples are sent, which laboratory may regularly communicate the results of the samples analysis back to the dairy farm (i.e. to the central processing and control device 19).

Alternatively, the processing and control device is connected to a measuring device for measuring a health-related parameter of the cows, and the processing and control device 19 is adapted to retrieve the health-related parameters and use them as the information regarding the health of each of the cows entering each station.

In FIG. 1 is illustrated an on-site measurement or analysis equipment 47 for measuring such a health-related parameter. The measurement equipment 47 may e.g. be a conductance-measuring device and/or an infrared spectrometer device for measuring the milk produced by each cow milked in the milking station 3. The measurement equipment may alternatively be comprised of any kind of on-site or on-line arrangement for automatic or semi-automatic milk analysis. By means of such milk analysis, for instance, the content of bacteria and spores, the content of sodium and potassium, the lactose concentration, and the somatic cell count value can be obtained. The measurement equipment 47 can be arranged to measure milk in the end unit 12, in the milk lines 13, or in the teat cups 11.

Alternatively, the on-site measurement equipment 47 may be an activity meter for measuring the activity of the cow (where an extraordinary high or low activity may indicate that the cow does not feel alright).

Other health-related parameters that may be measured, particularly automatically, at any of a milking station, a resting station or a feeding station include e.g. the milk amount produced by the cow, the feed consumption by the cow, the temperature of the cow and the weight of the cow.

Figure 3:
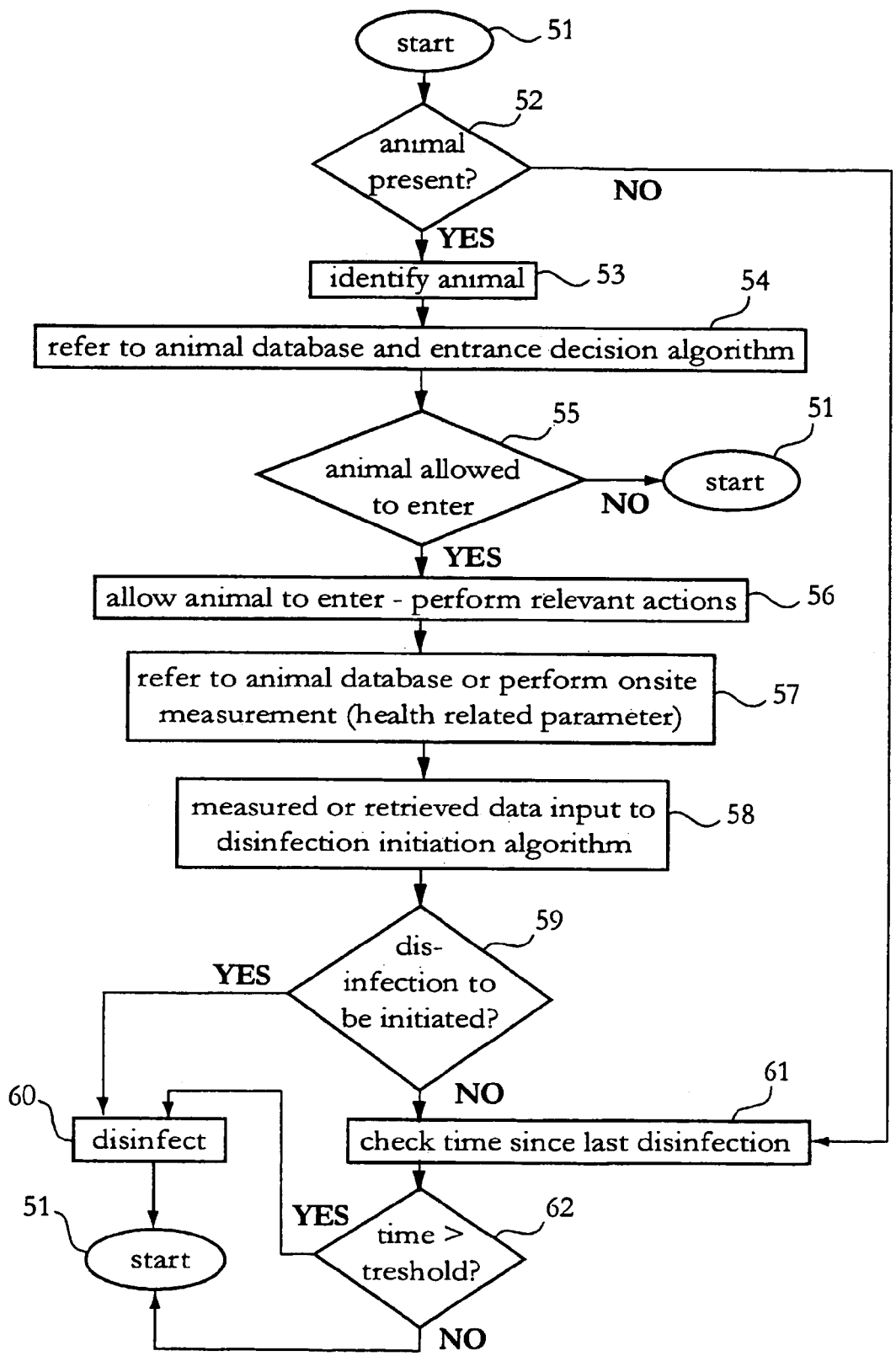
FIG. 3 illustrates, schematically, in a flow diagram a method according to a particular embodiment of the present invention.

With reference next to FIG. 3, which is a flow diagram of an algorithm for automatically disinfecting or sterilizing, which may be implemented in the central processing and control device 11 of the animal arrangement of FIG. 1, a particular embodiment of the present invention will be described. The algorithm will be exemplified as being implemented in the milking station 3, but may, mutatis mutandis, be implemented into any of the other stations of FIG. 1, or in fact in any other milking, feeding or resting station known in the art.

In a step 51, the algorithm is initiated, and in a step 52 it is checked whether a cow is present in front of the milking station 3. If the answer is negative the algorithm is continued with a step 61 to be described further below, and if the answer is affirmative, the cow is, in a step 53, identified.

Subsequently, a decision algorithm is, in a step 54, run to decide whether the cow identified shall be allowed to enter the milking station 3, where the decision algorithm may retrieve data from the database of FIG. 4. Then, it is, in a step 55, checked whether the cow is allowed to enter the station, and if the answer is negative the algorithm is returned to the initial step 51. If the answer is affirmative the inlet gate 4 is, in a step 56, opened and the cow is allowed to enter to be milked.

While the cow is prepared for milking and subsequently milked, the FIG. 3 algorithm refers, in a step 57, to the database and/or performs an on-site measurement of a health related parameter to retrieve data regarding the health of the cow, whereafter the data is, in a step 58, input into a disinfection initiation algorithm for deciding whether the data reveals that the cow has an infection, e.g. mastitis, that is capable of being transmitted to other cows.

Next, in a step 59 it is decided whether disinfection or sterilization shall be initiated and if so it is in a step 60 initiated, wherafter the algorithm is returned to the initial step 51. Note that step 60 shall not be performed until it has been assured that the cow has left the station. If disinfection or sterilization shall not be initiated it is, in a step 61, checked how long time has lapsed since disinfection or sterilization was last performed. This step is also performed directly after step 52 if there is no cow to visit the station 3.

The time lapsed is, in a step 62, compared with a threshold value and if the time lapsed is higher than the threshold value the algorithm is passed to the step 60 and initiates disinfection or sterilization, wherafter the algorithm is returned to the initial step 51. If the time lapsed is not higher than the threshold value, the algorithm is directly returned to the initial step 51.

Note that a lower threshold may be used if no cow is present in front of the milking station 3 since disinfection or sterilization in this instance does not affect the utilization of the milking station.

Further, the threshold value may be set depending on the percentage of the cows in the area 1 that have an infection capable of being transmitted to other milking animals, where the percentage is deduced from information retrieved from the database regarding the health of each of the cows in the area 1. By this provision it can be ensured that the station is disinfected or sterilized more often if there are a high number of infectious cows in the stock.

It will be obvious that the invention may be varied in a plurality of ways. Such variations are not to be regarded as a departure from the scope of the invention. All such modifications as would be obvious to one skilled in the art are intended to be included within the scope of the appended claims.

The invention claimed is:

1. A method of automatically disinfecting or sterilizing at least a portion of any of a resting, a milking, or a feeding station provided with an animal identification device and located in an area, in which milking animals are allowed to move, wherein each of said milking animals visiting said any of a resting, a milking, or a feeding station is identified, said method comprising:
   retrieving information regarding the health of each of said milking animals entering said any of a resting, a milking, or a feeding station;
   ascertaining the health of each said milking animal based on the retrieved information;
   automatically disinfecting or sterilizing said at least a portion of any of a resting, a milking, or a feeding station when it is ascertained that a milking animal entering said any of a resting, a milking, or a feeding station has an infection that is capable of being transmitted to other milking animals, the disinfection or the sterilization being performed after that said infectious milking animal has left said any of a resting, a milking, or a feeding station; and preventing further milking animals from to entering said any of a resting, a milking, or a feeding station until the disinfection or the sterilization has been performed.

2. The method of claim 1 wherein said any of a resting, a milking, or a feeding station is connected to a computer, which holds a database with information of said milking animals and their health; and said step of retrieving information is performed by means of referring to said database.

3. The method of claim 2 wherein said information regarding the health of said milking animals is entered manually into said database; or is entered automatically from a computer-connected measuring device for measuring a health-related parameter of said milking animals.

4. The method of claim 1 wherein a health-related parameter of each of said milking animals is measured by means of a measuring device connected to said any of a resting, a milking, or a feeding station; and said step of retrieving information is performed by means of referring to said measuring device.

5. The method of claim 1, wherein said step of automatically disinfecting or sterilizing said at least a portion of any of a resting, a milking, or a feeding station is performed irrespective of said information retrieved if the time elapsed since said at least a portion of any of a resting, a milking, or a feeding station was last disinfected or sterilized is above a threshold value.

6. The method of claim 5 comprising:

retrieving information regarding the health of each of said milking animals in said area; and setting said threshold value depending on the percentage of said milking animals in said area that have an infection capable of being transmitted to other milking animals, where said percentage is deduced from said information retrieved regarding the health of each of said milking animals in said area.

7. The method of claim 1, wherein said step of automatically disinfecting or sterilizing said at least a portion of any of a resting, a milking, or a feeding station is performed irrespective of said information retrieved if it is established that no milking animal visits, or is to visit, said any of a resting, a milking, or a feeding station.

8. The method of claim 1, wherein said step of automatically disinfecting or sterilizing said at least a portion of any of a resting, a milking, or a feeding station is performed by means of exposing said at least a portion of any of a resting, a milking, or a feeding station to any of heat, radiation, or a chemical.

9. The method of claim 8 wherein said step of automatically disinfecting or sterilizing said at least a portion of any of a resting, a milking, or a feeding station comprises the step of flushing said at least a portion of any of a resting, a milking, or a feeding station with a hot fluid.

10. The method of claim 8 wherein said step of automatically disinfecting or sterilizing said at least a portion of any of a resting, a milking, or a feeding station comprises the step of irradiating said at least a portion of any of a resting, a milking, or a feeding station with UV light.

11. The method of claim 1, wherein said at least a portion of any of a resting, a milking, or a feeding station includes surfaces of said any of a resting, a milking, or a feeding station, which an animal visiting said any of a resting, a milking, or a feeding station may contact for a specified purpose or accidentally.

12. The method of claim 1, wherein said any of a resting, a milking, or a feeding station includes a milking station; and said at least a portion thereof includes a respective teat receiving opening of each teat cup of the milking station; a respective teat receiving opening of each teat cleaning cup of the milking station, if any; teat cleaning brushes of the milking station, if any; a front portion of a robot arm of the milking station; and a manger of the milking station.

13. The method of claim 1, wherein said any of a resting, a milking, or a feeding station includes a feeding station; and said at least a portion thereof includes surfaces of a manger of the feeding station.

14. The method of claim 1, wherein said any of a resting, a milking, or a feeding station includes a resting station; and said at least a portion thereof includes a floor of the resting station.

15. The method of claim 1, wherein said any of a resting, a milking, or a feeding station includes each station located in said area that is provided with an animal identification device; and said at least a portion thereof includes all surfaces of each station an animal in said area may contact for a specified purpose or accidentally.

16. A device for automatically disinfecting or sterilizing at least a portion of any of a resting, a milking, or a feeding station provided with an animal identification device and located in an area, in which milking animals are allowed to move, wherein each of said milking animals visiting said any of a resting, a milking, or a feeding station is identified, comprising:

a processing and control device adapted to retrieve information regarding the health of each of said milking animals entering said any of a resting, a milking, or a feeding station; and a disinfecting or sterilizing apparatus capable of automatically disinfecting or sterilizing said at least a portion of any of a resting, a milking, or a feeding station, said disinfecting or sterilizing apparatus being connected to said processing and control device, wherein said processing and control device is adapted, provided that said information retrieved reveals that a milking animal entering said any of a resting, a milking, or a feeding station has an infection that is capable of being transmitted to other milking animals, to control said disinfecting or sterilizing apparatus to automatically disinfect or sterilize said at least a portion of any of a resting, a milking, or a feeding station after that said infectious milking animal has left said any of a resting, a milking, or a feeding station, and before further milking animals are admitted to enter said any of a resting, a milking, or a feeding station.

17. The device of claim 16 wherein said processing and control device holds a database with information regarding the health of each of said milking animals entering said any of a resting, a milking, or a feeding station, which information said processing and control device is adapted to retrieve.

18. The device of claim 17 wherein said processing and control device is connected to a measuring device for measuring a health-related parameter of said milking animals, and said processing and control device is adapted to retrieve said information regarding the health of each of said milking animals entering said any of a resting, a milking, or a feeding station in the form of said health-related parameter.

19. The device of claim 16 comprising
a measuring device for measuring a health-related parameter of said milking animals, wherein
said processing and control device is adapted to retrieve said information regarding the health of each of said milking animals entering said any of a resting, a milking, or a feeding station in the form of said health-related parameter.

20. The device of claim 16, wherein said processing and control device is adapted to control said disinfecting or sterilizing apparatus to automatically disinfect or sterilize said at least a portion of any of a resting, a milking, or a feeding station irrespective of said information retrieved if the time lapsed since disinfection or sterilization was last performed by said apparatus is above a threshold value.

21. The device of claim 20 wherein said threshold value is set depending on the percentage of said milking animals in said area that have an infection capable of being transmitted to other milking animals.

22. The device of claim 16 wherein said processing and control device is adapted to control said disinfecting or sterilizing apparatus to automatically disinfect or sterilize irrespective of said information retrieved if no milking animal visits, or is to visit, said any of a resting, a milking, or a feeding station.

23. The device of claim 16 wherein said disinfecting or sterilizing apparatus is any of a heat supply apparatus, a chemical supply apparatus, or a radiation exposure apparatus.

24. The device of claim 23 wherein said disinfecting or sterilizing apparatus is an apparatus for flushing said at least a portion of any of a resting, a milking, or a feeding station with a hot fluid.

25. The device of claim 16 wherein said at least a portion of any of a resting, a milking, or a feeding station includes surfaces of said any of a resting, a milking, or a feeding station, which an animal visiting said any of a resting, a milking, or a feeding station may contact for a specified purpose or accidentally.

* * * * *